United States Patent [19]
Elcrin et al.

[11] Patent Number: 4,561,798
[45] Date of Patent: Dec. 31, 1985

[54] TELESCOPIC CYLINDRICAL TUBE COLUMN

[75] Inventors: Alain Elcrin; Edmond Chambron, both of Paris, France

[73] Assignee: Thomson CSF, Paris, France

[21] Appl. No.: 468,685

[22] Filed: Feb. 22, 1983

[30] Foreign Application Priority Data

Mar. 9, 1982 [FR] France .................. 82 03940

[51] Int. Cl.[4] .............................................. F16B 7/10
[52] U.S. Cl. .................................. 403/109; 403/379; 308/3 R
[58] Field of Search ............. 403/109, 379; 308/3 R, 308/4 R

[56] References Cited

U.S. PATENT DOCUMENTS

3,175,085  3/1965  Avery .
4,458,545  7/1984  Chaki et al. .................. 308/3 R

FOREIGN PATENT DOCUMENTS

889157  6/1981  Belgium .
882607  3/1943  France .
1174662  11/1958  France .................. 384/26
916178  1/1963  United Kingdom .

*Primary Examiner*—Andrew V. Kundrat
*Attorney, Agent, or Firm*—Cushman, Darby & Cushman

[57] ABSTRACT

A telescopic cylindrical tube column in which a first tube is fitted into a second tube. Rollers integral with the first tube engage opposite edges of each of a plurality of openings parallel to the longitudinal axis of the column to interlock the tubes. The rollers are fixed to the first tube at points different from their axis of rotation to allow adjustment of the position thereof.

4 Claims, 2 Drawing Figures

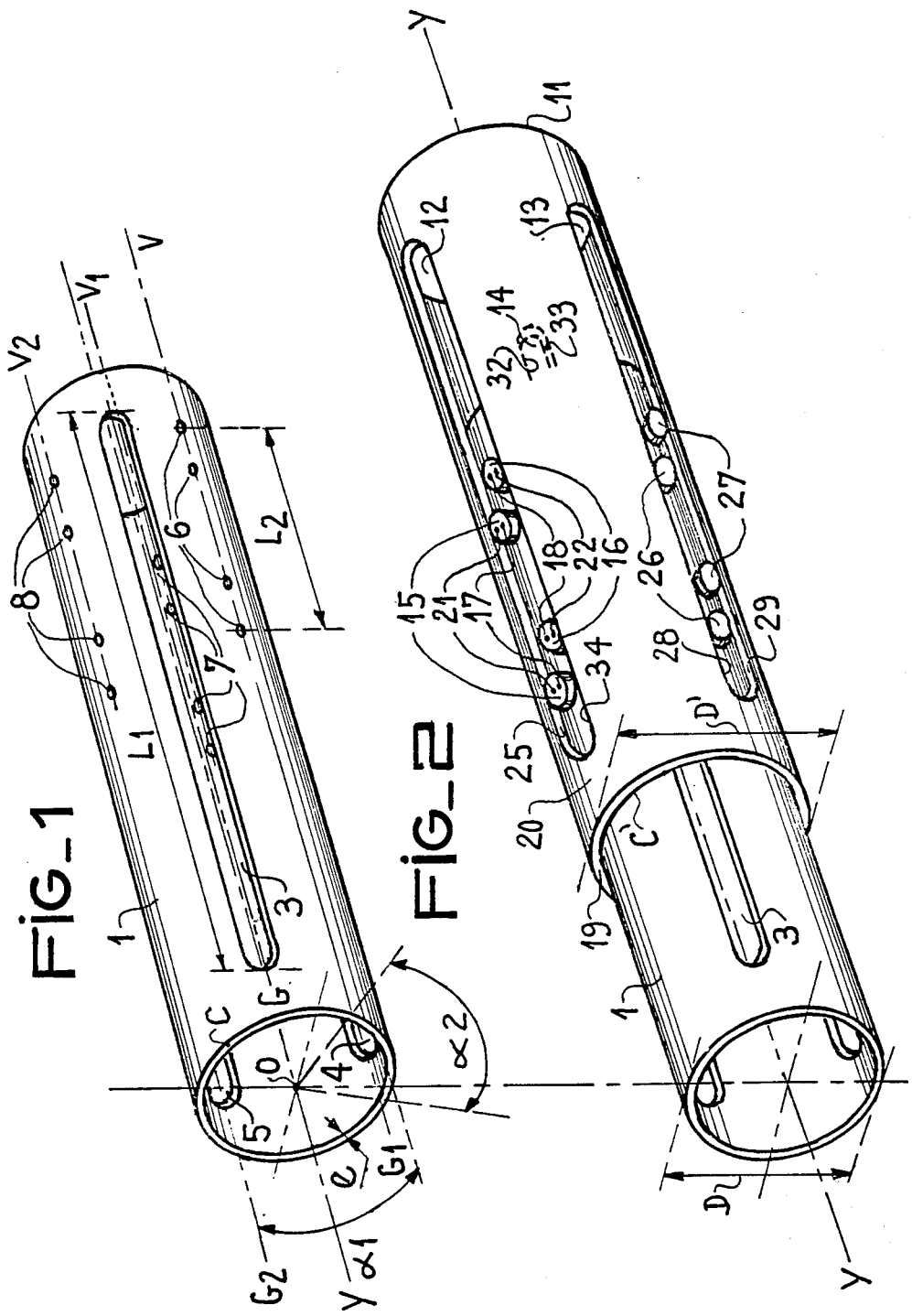

TELESCOPIC CYLINDRICAL TUBE COLUMN

BACKGROUND OF THE INVENTION

The invention relates to a telescopic cylindrical tube column able to be used in numerous fields such for example as radiology, where telescopic columns allow the X-ray emitting assemblies or detector assemblies which they support to be positioned.

These assemblies often form very heavy loads, connected to the telescopic column through an arm; this latter generally forms an angle of 90° with a longitudinal axis of the telescopic column, about which it is able to rotate, for positioning the load; this arrangement tends to make even more difficult the working conditions of these columns whose rigidity is maintained because of their massive structure, taking up a relatively large space.

Telescopic columns are generally formed from several tubes of different sections, adapted to slide in each other through the presence of linear guide means disposed over the length of these tubes between each of them.

These guide means may comprise for example four rails provided between each tube, on the periphery of which these rails are disposed spaced apart by 90°. One condition for proper sliding of the tubes resides in the parallelism of the rails; this parallelism is obtained by adjusting the position of these rails, such as adjustment of the parallelism of the first two opposing rails along a first axis of the section of a tube, followed by adjustment of the parallelism of the second rails situated on a second axis spaced at 90° from the first one.

This represents a long and delicate operation which forms a disadvantage. Another disadvantage of this arrangement resides in the fact that it does not lend itself to the use of cylindrical tubes, which tends to further increase the space occupied by the telescopic column thus formed. It should also be noted that in operation, when the arm carrying a load passes through the first axis on which the first rails are located, only the guide means comprising the second rails are in a position to withstand the forces created by this load.

Another type of guide means comprises balls rolling between two tubes, in longitudinal grooves; these latter are situated opposite each other, on the one hand on the inner wall of a first tube and, on the other hand, on the outer wall of a second tube sliding in the first one.

The drawback of this arrangement is that no adjustment is possible, more particularly when play appears between the tubes due to the wear of the grooves.

SUMMARY OF THE INVENTION

The present invention provides a telescopic column formed from cylindrical tubes, comprising means arranged so that the operations for assembling and aligning such a telescopic column are facilitated; the combination of these means allows a low cost, space-saving telescopic column to be formed whose characteristics may be maintained after prolonged use by providing more especially easy access to the linear guide means.

The present invention provides then a telescopic cylindrical tube column, comprising at least a first and a second tube forming respectively with respect to each other an inner tube and an outer tube, the first tube being able to be fitted in the second one along a longitudinal axis, wherein the second tube comprises at least three openings, parallel to this axis and disposed symmetrically on the circumference of this tube, in which are engaged first rolling means integral with the first tube, these first rolling means and these openings cooperating to interlock the first and the second tubes and to provide guiding for these tubes allowing them to move with respect to each other parallel to the longitudinal axis. The rolling means are fixed to the first tube at points different from their axis of rotation to allow adjustment of the position thereof.

BRIEF DESCRIPTION OF THE DRAWINGS

The invention will be better understood from the following description and the accompanying figures in which:

FIG. 1 shows in a perspective view a first section of a telescopic column in accordance with the invention;

FIG. 2 shows in a perspective view a telescopic column in accordance with the invention.

FIG. 1 shows a first cylindrical tube 1 forming a first section of a telescopic column 2 in accordance with the invention shown in FIG. 2.

For the sake of clarity the same elements bear the same references throughout the figures.

DESCRIPTION OF THE PREFERRED EMBODIMENTS

The first tube 1 shown in FIG. 1 comprises rectilinear openings 3,4,5 formed over a length L1 of its wall 9, through the whole thickness e thereof. In the non limiting example described, these openings 3,4,5 are at least three in number, spaced apart symmetrically over the circumference C of tube 1, parallel to longitudinal axis Y—Y of this latter, along axes respectively G, G1, G2; also according to the example described, the positions of these axes with reference to a center O of circumference C, form therebetween angles equal to 120° such as angle $\alpha1$ between axis G1 and axis G2.

Wall 9 also comprises, over a length L2 less than length L1, fixing means formed in the non limiting example described by:

a first series of four tapped holes 6 aligned along an axis V, a second series of four tapped holes 7 aligned along an axis V1, a third series of four tapped holes 8 aligned along an axis V2.

The axes V, V1, V2 are parallel to the longitudinal axis Y—Y and are symmetrically spaced apart over circumference C between axes G, G1, G2, with respect to which they are offset by 60° such as angle $\alpha2$ formed between the position of axis V and axis G1.

These holes 6,7,8 are for fixing first rolling means such for example as two rollers 15 and for fixing second rolling means such as two rollers 16; these rollers 15,16 being shown in FIG. 2.

FIG. 2 shows a telescopic column 2 in accordance with the invention, comprising a second tube 11 in which is partially fitted the first tube 1 already described; these tubes 1, 11 form with respect to each other an inner tube 1 and an outer tube 11.

The present description of the first tube 1 is also valid for the second tube 11 and for N additional tubes not shown, the only difference involving their diameter D,D' or DN, required for fitting these tubes 1,11,N into each other; furthermore, this representation of a telescopic column 2 in accordance with the invention is not limiting, since it may comprise N additional tubes not shown for clarity of the description.

The second tube 11 comprises three openings 12, 13, 14 identical to openings 3, 4, 5 in tube 1 already described, opening 14 being shown with broken lines in FIG. 2; these openings form rolling paths.

Rollers 15,16 engaged in opening 12 are integral with the first tube 1 to which they are fixed by conventional means, not shown, such as screws for example cooperating with holes 6 shown in FIG. 1.

These rollers 15,16 are able to be fixed eccentrically, this arrangement being obtained in the non limiting example described because their fixing points 17,18 are different from their center, respectively 21,22. Thus, both rollers 15 forming first rolling means may be positioned so that they bear on a first edge 25 of opening 12 and rollers 16 forming second rolling means may be positioned so that they bear on the second edge 34 of this same opening. The same goes for opening 13 in which two other first rolling means are engaged such as rollers 26 and two other second rolling means such as rollers 27, integral with the first tube 1; the second rollers 26 bear on a first edge 28 of opening 13, and the two rollers 27 bear on the second opposite edge 29 of this same opening 13. Four rollers, not shown in FIG. 2, are also integral with the first tube 1 and cooperate with opening 14 having a first and a second edge 32,33, under the same conditions as those just explained.

These rollers are thus capable of rolling on these edges formed by the thickness 19 of wall 20 of the second tube 11.

This combination of means provides guiding by means of which:

tubes 1 and 11 are able to be moved with respect to each other parallel to the longitudinal axis Y—Y, tubes 1 and 11 are interlocked together and centered with respect to each other during construction rapidly and easily.

During construction, rollers 15,16,26,27 . . . are fixed to tube 1 through openings 12,13,14 of the second tube, in which the first tube is then already engaged; this facilitates the centering and aligning operations and allows, by adjusting the position of these rollers, to take up the play due to the manufacturing tolerances of the tubes, to machining tolerances and to wear due to operation.

Another advantage consists in the fact that a telescopic column 1 in accordance with the invention, since it is formed with cylindrical sections such as tubes 1, 11 . . . etc. takes up less space and has improved mechanical resistance with respect to the stresses exerted by a load (not shown), compared with telescopic columns constructed according to the prior art; this is due, in so far as the mechanical strength is concerned; to a better distribution of the connecting points between tube 1 and tube 11, such as formed by openings 12,13,14 in tube 11, formed at 120° from each other on the circumference C', cooperating with the first and second rolling means, shown by rollers 15,26 . . . etc. and 26,27 . . . etc.—and in so far as the space required is concerned: to the fact that cylindrical tubes 1,11 are used, whose wear can be taken up contrary to the cylindrical tubes formed according to the prior art, and in that the rolling means formed by rollers 15,16 . . . etc fulfill their function within the thickness 19 of tube 11. It should be noted that, for example, the first rolling means 15,26 . . . , with a sufficient diameter, could fulfill this function alone, but that the presence of at least one roller 16,27 . . . per opening 12,13,14 considerably facilitates the assembly and adjustment operations.

In the non limiting example of the description, the second tube 11, forming a last outer tube, does not comprise any rollers (not shown); if it were thus provided, these rollers would allow it to cooperate with a third tube which would be external (not shown) under the same conditions as those in which the first tube 1 cooperates with the second tube 11.

Similarly, the first tube 1 comprises openings 3,4, 5 in which could be engaged rollers integral with the fourth tube (not shown), this fourth tube then cooperating with the first tube 1 under the same conditions as the cooperation between tube 1 and tube 11.

What is claimed is:
1. A telescopic cylindrical tube column comprising:
   a first tube;
   a second tube with said first tube fitted therein along a longitudinal axis and having at least three openings parallel to said axis and disposed symmetrically about the circumference of said second tube;
   first and second rolling means each fixed to said first tube at points different from their center of rotation to allow adjustment of the position thereof and cooperating with said opening to interconnect said first and second tubes and guide movement of said tubes with respect to each other parallel to said axis, said first rolling means each bearing on one edge of an opening and said second rolling means bearing on the opposite edge.
2. The telescopic column as claimed in claim 1, wherein said openings which form rolling paths are formed in the whole thickness of the wall which the second tube comprises, allowing access to said rolling means.
3. The telescopic column as claimed in claim 1, wherein said openings are spaced apart at angles equal to 120°.
4. The telescopic column as claimed in claim 1, wherein said first and second tubes are interlocked in positions such that their openings are offset respectively by an angle of 60°.

* * * * *